(12) United States Patent
Bouix-Peter et al.

(10) Patent No.: US 8,729,312 B2
(45) Date of Patent: May 20, 2014

(54) DERIVATIVES OF NOVEL PEROXIDES, METHOD OF PREPARATION THEREOF AND USE THEREOF IN HUMAN MEDICINE AS WELL AS IN COSMETICS FOR THE TREATMENT OR PREVENTION OF ACNE

(75) Inventors: Claire Bouix-Peter, Vallauris (FR); Jean-Claude Pascal, Nice (FR); Nicolas Rodeville, Biot (FR)

(73) Assignee: Galderma Research & Development, Biot (FR)

( * ) Notice: Subject to any disclaimer, the term of this patent is extended or adjusted under 35 U.S.C. 154(b) by 53 days.

(21) Appl. No.: 13/514,262

(22) PCT Filed: Dec. 10, 2010

(86) PCT No.: PCT/EP2010/069421
§ 371 (c)(1),
(2), (4) Date: Aug. 15, 2012

(87) PCT Pub. No.: WO2011/070171
PCT Pub. Date: Jun. 16, 2011

(65) Prior Publication Data
US 2013/0178648 A1    Jul. 11, 2013

(30) Foreign Application Priority Data
Dec. 10, 2009  (FR) ..................... 09 58847

(51) Int. Cl.
*C07C 409/00* (2006.01)
(52) U.S. Cl.
USPC .......................... 568/566; 568/558

(58) Field of Classification Search
USPC ................................. 568/566, 558
See application file for complete search history.

(56) References Cited

U.S. PATENT DOCUMENTS 4,364,940 A * 12/1982 Neiss et al. .................... 514/533

OTHER PUBLICATIONS

Evanochko et al., "Investigation of o-Acetoxyaryl Radicals", J. Org. Chem., Jan. 1, 1979, pp. 4426-4430, vol. 44, No. 24, American Chemical Society.

* cited by examiner

*Primary Examiner* — Johann R Richter
*Assistant Examiner* — Amy C Bonaparte
(74) *Attorney, Agent, or Firm* — Dentons US LLP

(57) ABSTRACT

Compounds of the following general formula (I):

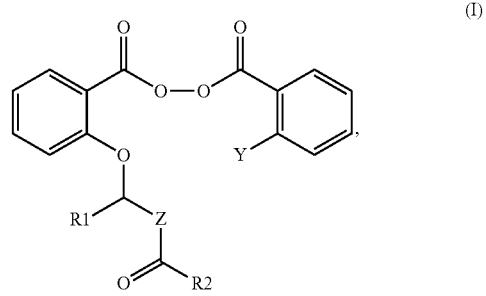

are described. Also described, are methods of preparing the compounds and their use in therapeutics.

9 Claims, No Drawings

DERIVATIVES OF NOVEL PEROXIDES, METHOD OF PREPARATION THEREOF AND USE THEREOF IN HUMAN MEDICINE AS WELL AS IN COSMETICS FOR THE TREATMENT OR PREVENTION OF ACNE

CROSS-REFERENCE TO PRIOR APPLICATIONS

This application is a National Stage of PCT/EP2010/069421, filed Dec. 10, 2010, and designating the United States (published in the English language on Jun. 16, 2011, as WO 2011/070171 A1; the title and abstract were also published in English), which claims priority of FR 0958847, filed Dec. 10, 2009, each hereby expressly incorporated by reference in its entirety and each assigned to the assignee hereof.

Acne affects 90% of all adolescents, but also men and women in their twenties or thirties, or it may even persist throughout adulthood. The process of development of acne is described by W. J. Cunliffe in "New Approaches to Acne Treatment", published by Martin Dunitz, London, 1989.

Common acne (acne vulgaris) is a chronic disorder of the pilosebaceous follicles (pilosebaceous apparatus) that is characterized by comedones (blackheads), papules, pustules, cysts, nodules and often scars which appear on the most visible areas of the skin, notably on the face, chest, back and sometimes the neck and upper arms.

The pilosebaceous apparatus is largely under the control of endogenous hormones (mainly androgens) which are present at unusually high concentrations in the blood during adolescence and puberty and result in excessive production of sebum. This situation may worsen as a result of a concomitant increase in the degree of keratinization of the horny layer of the skin (stratum corneum). As the horny cells proliferate, they can form an occlusive plug or comedo which, combined with increased production of sebum, constitutes an ideal medium for proliferation of the strains of bacteria that reside on and in the skin, such as the Gram-positive anaerobic bacterium *Propionibacterium acnes*.

The exposed follicles can darken in colour through deposition of pigment derived from damaged cells of the deep layer of the skin.

Acne is a condition with several stages, and in its most serious form it leads to hospitalization of the patient and proves very troublesome with long-term presence of scarring of the skin.

There is a need for improved treatments of acne that effectively prevent the condition progressing to its most severe form and that can be used without adverse effects by the majority of persons afflicted.

At present, numerous treatments are available for treating acne but unfortunately each treatment has limitations that it would be desirable to overcome.

In most cases, treatment of acne employs topical formulations in the form of creams, gels, emulsions or lotions containing selected agents.

These agents comprise, for example, hormones or agonists and antagonists of hormones (EPA1 0 563 813 and U.S. Pat. No. 5,439,923), antimicrobial agents (U.S. Pat. No. 4,446,145, GB 2 088 717, GB 2 090 135, GB 1 054 124, U.S. Pat. No. 5,409,917), salicylic acid (U.S. Pat. Nos. 4,514,385, 4,355,028, EPA1 0 052 705, FR-A 2 581 542 and FR-A 2 607 498).

The problems associated with topical treatment of acne with creams, gels, emulsions or lotions comprise lack of precision in application and absence of precise control of the dose at the intended site. Application of a cream, gel, emulsion or lotion involves exposing an area considerably larger than that covered by the lesion, so normal healthy skin is exposed to the anti-acne formulation. Salicylic acid, for example, is irritant to normal skin in the case of prolonged exposure, notably at high concentrations.

Oral administration of anti-acne agents is commonly envisaged in severe cases of acne. These are reviewed by Sykes N. I. and Webster G. In "Acne, A Review of Optimum Treatment", Drugs 48, 59-70 (1994). Numerous side effects have been described in the administration of anti-acne active compounds by the oral route.

For example, isotretinoin, which is a derivative of vitamin A, has associated risks of teratogenicity and it can constitute a risk for women of child-bearing age.

The oral administration of antibiotics suitable for the treatment of acne may be accompanied by the development of side effects such as abdominal cramps, glossophytia, cough, diarrhoea, fatigue, mouth irritation and other undesirable symptoms.

There is therefore a clear medical and cosmetic need for treatment of the disorders and associated pathologies.

In this context, the present invention proposes to provide novel derivatives of peroxides having improved anti-acne efficacy resulting for example from better bactericidal activity than the compounds of the prior art such as benzoyl peroxide, while controlling the potential sensitizing effect, the irritant effect, and not adding a component with anti-inflammatory activity.

Thus, the present invention relates to compounds of the following general formula (I):

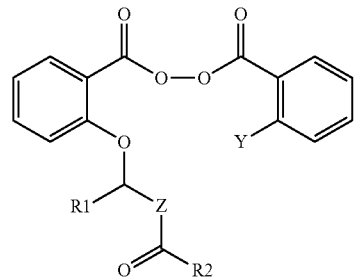

in which:

Z represents an oxygen or the following sequence:

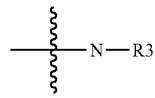

Y represents a hydrogen or the following sequence:

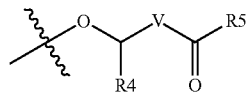

V represents an oxygen or the following sequence:

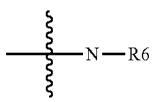

R3 and R6 represent, identically or independently, a hydrogen or a $C_{1-4}$ alkyl R1 and R4 represent, identically or independently, a hydrogen or a $C_{1-4}$ alkyl R2 and R5 represent, identically or independently, a $C_{1-10}$ alkyl or a $C_{1-10}$ alkoxy According to the present invention, the preferred compounds corresponding to general formula (I) are those having the following characteristics:

Z represents an oxygen or the following sequence:

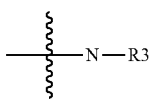

Y represents a hydrogen or the following sequence:

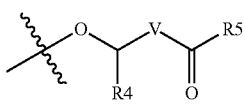

V represents an oxygen or the following sequence:

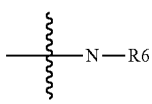

R3 and R6 represent, identically or independently, a hydrogen, a methyl or an ethyl R1 and R4 represent, identically or independently, a hydrogen or a methyl R2 and R5 represent, identically or independently, a $C_{1-4}$ alkyl or a $C_{1-4}$ alkoxy According to the present invention, $C_{1-4}$ alkyl denotes a saturated, linear or branched hydrocarbon chain comprising 1 to 4 carbon atoms.

According to the present invention, $C_{1-10}$ alkyl denotes a saturated, linear or branched hydrocarbon chain comprising 1 to 10 carbon atoms.

According to the present invention, $C_{1-4}$ alkoxy denotes an oxygen atom substituted with a $C_{1-4}$ alkyl.

According to the present invention, $C_{1-10}$ alkoxy denotes an oxygen atom substituted with a $C_{1-10}$ alkyl.

Among the compounds of general formula (I) coming within the scope of the present invention, we may notably mention the following:

Example 1: bis(2-acetoxymethoxy)-benzoyl peroxide
Example 2: (2-acetoxymethoxy-benzoyl)benzoyl peroxide
Example 3: bis(2-propionyloxymethoxy)-benzoyl peroxide
Example 4: (2-propionyloxymethoxy-benzoyl)benzoyl peroxide
Example 5: bis(2-butyryloxymethoxy)-benzoyl peroxide
Example 6: (2-butyryloxymethoxy-benzoyl)benzoyl peroxide
Example 7: bis(2-pentanoyloxymethoxy)-benzoyl peroxide
Example 8: (2-pentanoyloxymethoxy-benzoyl)benzoyl peroxide
Example 9: bis(2-isobutyryloxymethoxy)-benzoyl peroxide
Example 10: (2-isobutyryloxymethoxy-benzoyl)benzoyl peroxide
Example 11: bis[2-(2,2-dimethyl-propionyloxymethoxy)]-benzoyl peroxide
Example 12: [2-(2,2-dimethyl-propionyloxymethoxy)-benzoyl]benzoyl peroxide
Example 13: bis[2-(1-acetoxy-ethoxy)]-benzoyl peroxide
Example 14: [2-(1-acetoxy-ethoxy)-benzoyl]benzoyl peroxide
Example 15: bis(2-ethoxycarbonyloxymethoxy)-benzoyl peroxide
Example 16: (2-ethoxycarbonyloxymethoxy-benzoyl) benzoyl peroxide
Example 17: bis(2-propoxycarbonyloxymethoxy)-benzoyl peroxide
Example 18: (2-propoxycarbonyloxymethoxy-benzoyl)benzoyl peroxide
Example 19: bis(2-butoxycarbonyloxymethoxy)-benzoyl peroxide
Example 20: (2-butoxycarbonyloxymethoxy-benzoyl)benzoyl peroxide
Example 21: bis(2-isopropoxycarbonyloxymethoxy)-benzoyl peroxide
Example 22: (2-isopropoxycarbonyloxymethoxy-benzoyl) benzoyl peroxide
Example 23: bis(2-tert-butoxycarbonyloxymethoxy)-benzoyl peroxide
Example 24: (2-tert-butoxycarbonyloxymethoxy-benzoyl) benzoyl peroxide
Example 25: bis[2-(ethoxycarbonylamino-methoxy)]-benzoyl peroxide
Example 26: [2-(ethoxycarbonylamino-methoxy)-benzoyl] benzoyl peroxide
Example 27: bis(2-[(ethoxycarbonyl-ethyl-amino)-methoxy])-benzoyl peroxide
Example 28: (2-[(ethoxycarbonyl-ethyl-amino)-methoxy]-benzoyl)benzoyl peroxide
Example 29: bis(2-[(ethoxycarbonyl-methyl-amino)-methoxy])-benzoyl peroxide
Example 30: (2-[(ethoxycarbonyl-methyl-amino)-methoxy]-benzoyl)benzoyl peroxide
Example 31: bis(2-[(methyl-propoxycarbonyl-amino)-methoxy])-benzoyl peroxide
Example 32: (2-[(methyl-propoxycarbonyl-amino)-methoxy]-benzoyl)benzoyl peroxide
Example 33: bis(2-[(butoxycarbonyl-methyl-amino)-methoxy])-benzoyl peroxide
Example 34: (2-[(butoxycarbonyl-methyl-amino)-methoxy]-benzoyl)benzoyl peroxide
Example 35: bis(2-[(isopropoxycarbonyl-methyl-amino)-methoxy])-benzoyl peroxide
Example 36: (2-[(isopropoxycarbonyl-methyl-amino)-methoxy]-benzoyl)benzoyl peroxide
Example 37: bis(2-[(tert-butoxycarbonyl-methyl-amino)-methoxy])-benzoyl peroxide
Example 38: (2-[(tert-butoxycarbonyl-methyl-amino)-methoxy]-benzoyl)benzoyl peroxide
Example 39: bis[2-(1-ethoxycarbonyloxy-ethoxy)]-benzoyl peroxide
Example 40: [2-(1-ethoxycarbonyloxy-ethoxy)-benzoyl] benzoyl peroxide A general description of methods of preparation of the compounds of formula (I) is given below. In these schemes and in the following description of the method, unless specified otherwise, all the substituents are as defined for the compounds of formula (I).

In the case when group Y defined in formula (I) is a hydrogen, the compounds of general formula (I) are prepared following reaction scheme 1 or reaction scheme 2 presented below.

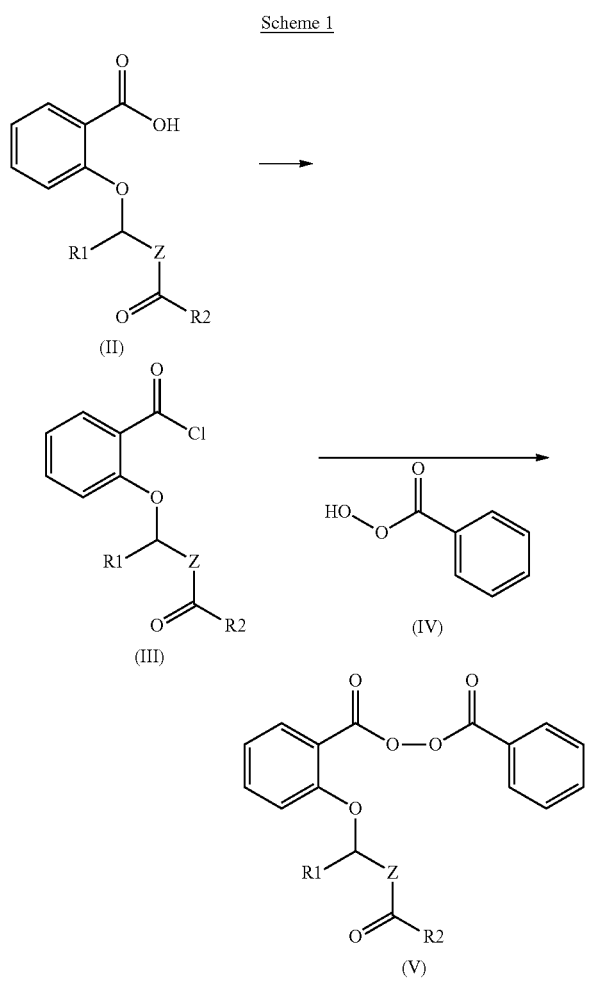

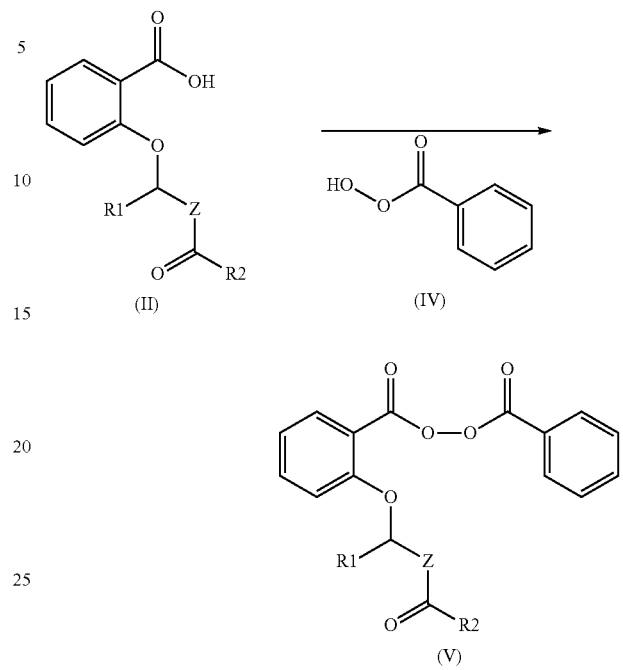

According to scheme 1, the acid chlorides of general formula (III) are prepared from carboxylic acid (II), by methods selected from those known by a person skilled in the art (EP 121 968 2). They comprise the use of thionyl chloride and pyridine in a solvent such as toluene or dichloromethane for example.

The carboxylic acids of general formula (II) are prepared according to the methods described in scheme 7.

In a final stage, the compounds of general formula (V) can be prepared by coupling between the acyl chlorides of formula (III) and the per-acid of formula (IV), using pyridine as base in a mixture of solvents such as dichloromethane and chloroform (Evanochko, W. T.; Shevlin, P. B.; *J. Org. Chem.* 1979, 44(24), 4426-4430).

The per-acid of general formula (IV) is prepared according to the method described in scheme 8 from benzoyl peroxide.

According to scheme 2, the peroxides of general formula (V) are prepared by coupling between the carboxylic acids of formula (II) and the per-acid of formula (IV), for example using N,N'-dicyclohexylcarbodiimide as coupling agent for example in a mixture of solvents such as diethyl ether and dichloromethane (Spantulescu, M. D.; Jain, R. P.; Derksen, D. J.; Vederas, J. C.; *Org. Lett.* 2003, 5(16), 2963-2965).

The carboxylic acids of general formula (II) are prepared according to the methods described in scheme 7.

The per-acid of general formula (IV) is prepared according to the method described in scheme 8 from benzoyl peroxide.

In the case when group Y defined in formula (I) is not a hydrogen, when group R1 defined in formula (I) is identical to group R4, when group R2 defined in formula (I) is identical to group R5, and when group Z defined in formula (I) is identical to group V, the compounds of general formula (I) are prepared following reaction scheme 3 or reaction scheme 4 presented below.

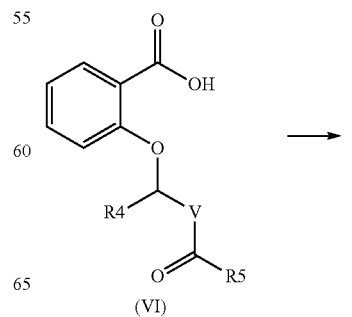

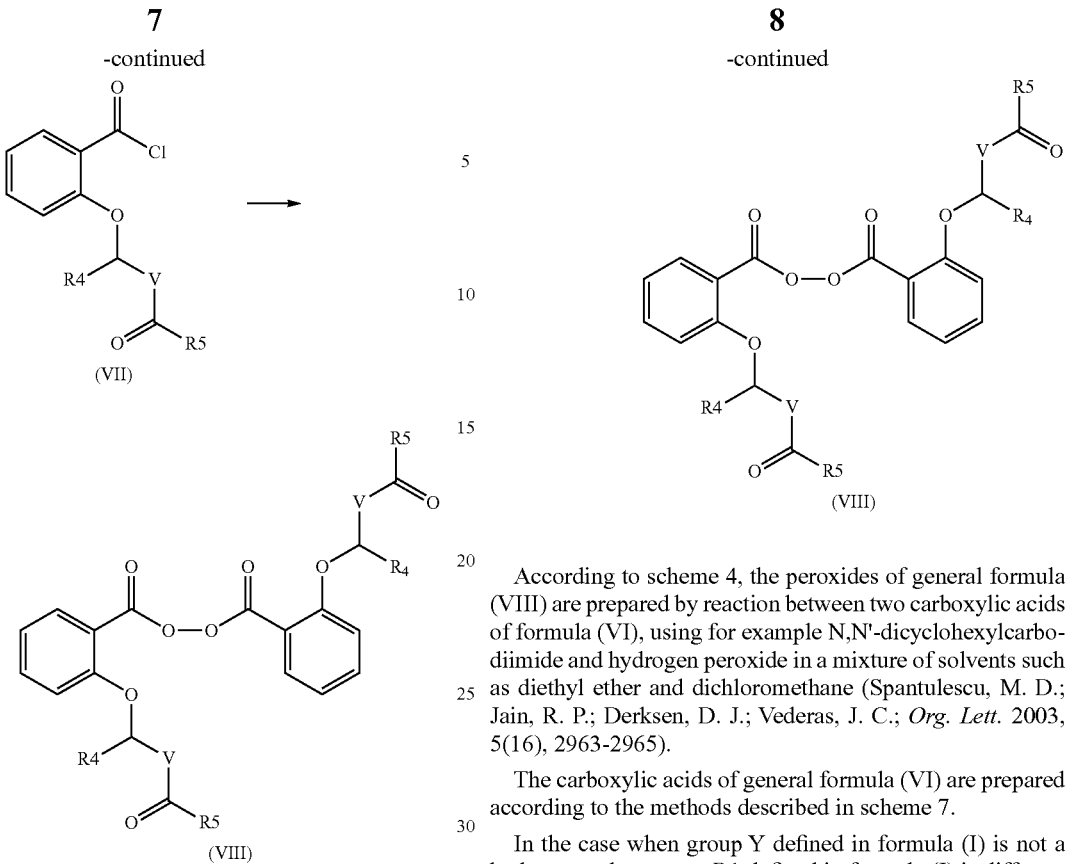

(VII)

(VIII)

According to scheme 3, the acid chlorides of general formula (VII) are prepared from carboxylic acid (VI), by methods selected from those known by a person skilled in the art (EP 121 968 2). They comprise the use of thionyl chloride and pyridine in a solvent such as toluene or dichloromethane for example.

The carboxylic acids of general formula (VI) are prepared according to the methods described in scheme 7.

In a final stage, the compounds of general formula (VIII) can be prepared by coupling between two acyl chlorides of formula (VII) by methods selected from those known by a person skilled in the art (EP 0 108 821). They comprise the use of hydrogen peroxide and sodium bicarbonate in a solvent such as tetrahydrofuran for example.

Scheme 4

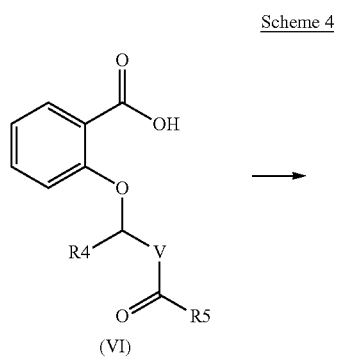

(VI)

According to scheme 4, the peroxides of general formula (VIII) are prepared by reaction between two carboxylic acids of formula (VI), using for example N,N'-dicyclohexylcarbodiimide and hydrogen peroxide in a mixture of solvents such as diethyl ether and dichloromethane (Spantulescu, M. D.; Jain, R. P.; Derksen, D. J.; Vederas, J. C.; *Org. Lett.* 2003, 5(16), 2963-2965).

The carboxylic acids of general formula (VI) are prepared according to the methods described in scheme 7.

In the case when group Y defined in formula (I) is not a hydrogen, when group R1 defined in formula (I) is different from group R4, when group R2 defined in formula (I) is different from group R5, and when group Z defined in formula (I) is different from group V, the compounds of general formula (I) are prepared following reaction scheme 5 or reaction scheme 6 presented below.

Scheme 5

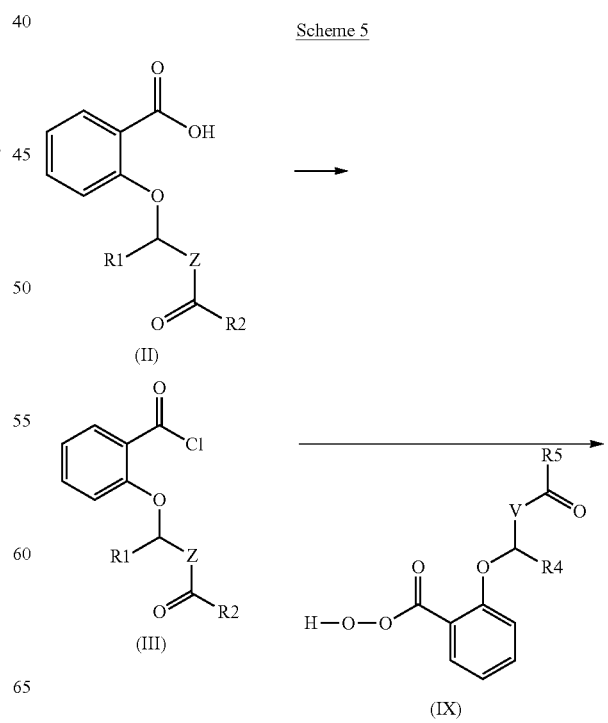

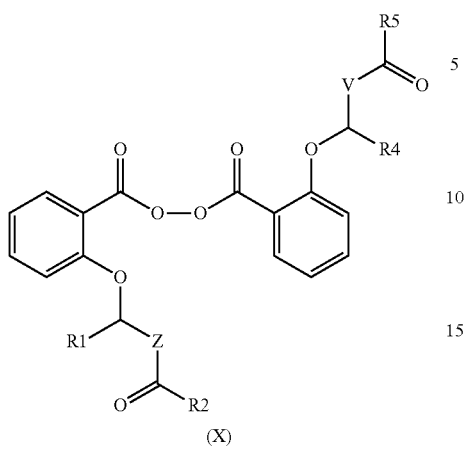

(X)

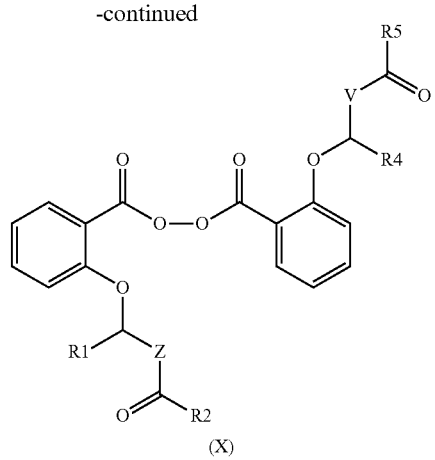

(X)

According to scheme 5, the acid chlorides of general formula (III) are prepared from carboxylic acid (II), by methods selected from those known by a person skilled in the art (EP 121 968 2). They comprise the use of thionyl chloride and pyridine in a solvent such as toluene or dichloromethane for example.

The carboxylic acids of general formula (II) are prepared according to the method described in scheme 7.

In a final stage, the compounds of general formula (X) can be prepared by coupling between the acyl chlorides of formula (III) and the per-acid of formula (IX), for example using pyridine as base in a mixture of solvents such as dichloromethane and chloroform.

The per-acid of general formula (IX) is prepared according to the method described in scheme 9 from the peroxide defined in formula (VIII).

According to scheme 6, the peroxides of general formula (X) are prepared by coupling between the carboxylic acids of formula (II) and the per-acid of formula (IX), for example using N,N'-dicyclohexylcarbodiimide as coupling agent in a mixture of solvents such as diethyl ether and dichloromethane.

The carboxylic acids of general formula (II) are available commercially or are prepared according to the method described in scheme 7.

The per-acid of general formula (IX) is prepared according to the method described in scheme 9 from the peroxide defined in formula (VIII).

The carboxylic acids of formula (II) can be prepared according to reaction scheme 7. The carboxylic acids of formula (VI) are prepared according to the same reaction scheme.

Scheme 7

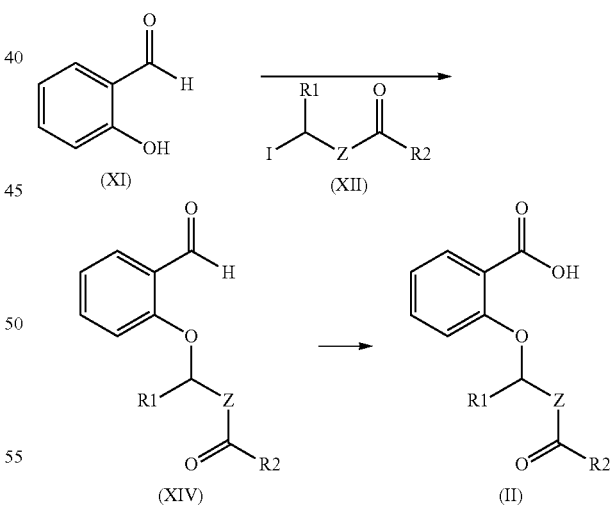

Scheme 6

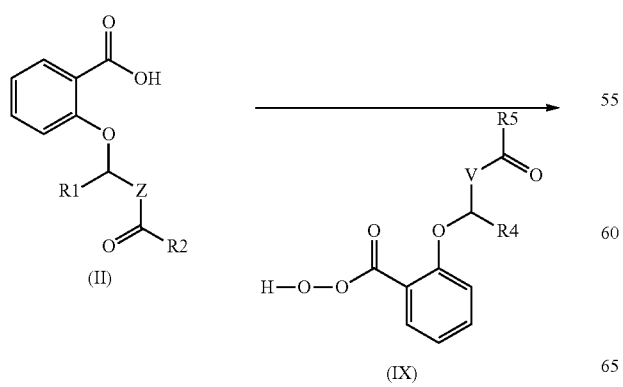

According to scheme 7, the aldehydes of formula (XIV) are prepared from salicylaldehyde (XI) by methods selected from those known by a person skilled in the art (Thomas, J. D.; Sloan, K. B.; *Tetrahedron Lett.* 2007, 48, 109-112). They comprise the use of a halide of formula (XII) or (XIII) and bases such as triethylamine, pyridine, potassium carbonate in a solvent such as acetone or dichloromethane for example.

In a final stage, the carboxylic acids of general formula (II) can be prepared by oxidation of the aldehydes of formula (XIV) with sodium perchlorite, in a mixture of solvents such as water and tert-butanol (Marsini, M. A.; Gowin, K. M.; Pettus, T. R. R.; *Org. Lett.* 2006, 8 (16), 3481-3483).

The per-acid of formula (IV) can be prepared according to reaction scheme 8.

Scheme 8

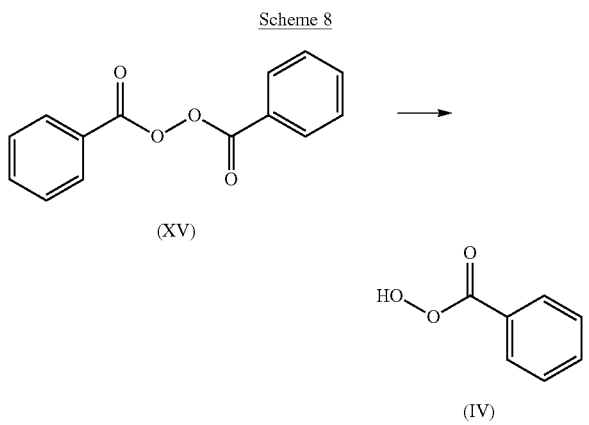

(XV)

(IV)

According to scheme 8, the per-acid of formula (IV) is prepared from dibenzoyl peroxide (XV) by methods selected from those known by a person skilled in the art (U.S. Pat. No. 3,075,921). They comprise the use of a peroxide (XV) and sodium in a mixture of solvents such as methanol and chloroform.

The per-acids of formulae (IX) can be prepared according to reaction scheme 9.

Scheme 9

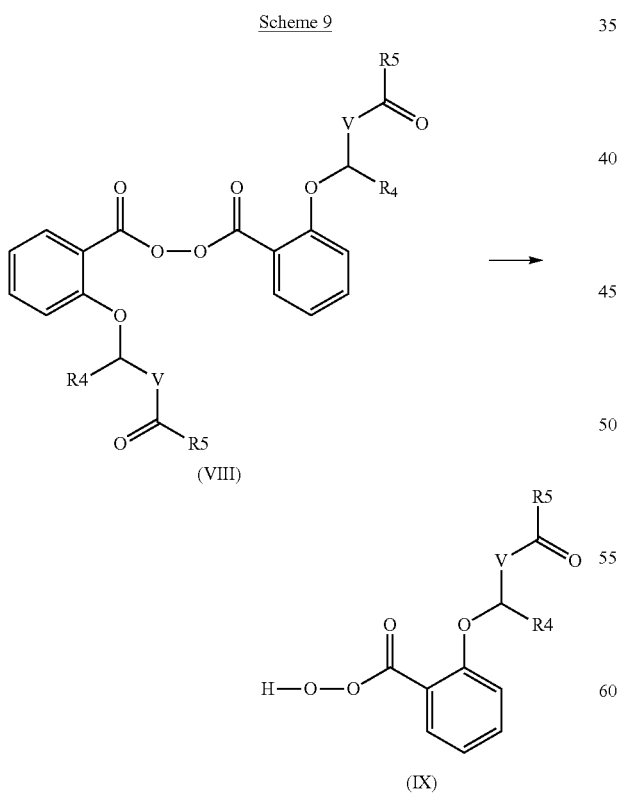

(VIII)

(IX)

According to scheme 9, the per-acids of formula (IX) are prepared from the peroxide of formula (VIII) by methods selected from those known by a person skilled in the art (U.S. Pat. No. 3,075,921). They comprise the use of a peroxide (VIII) and sodium in a mixture of solvents such as methanol and chloroform.

The iodides of formula (XII) can be prepared according to reaction scheme 10 or are available commercially.

Scheme 10

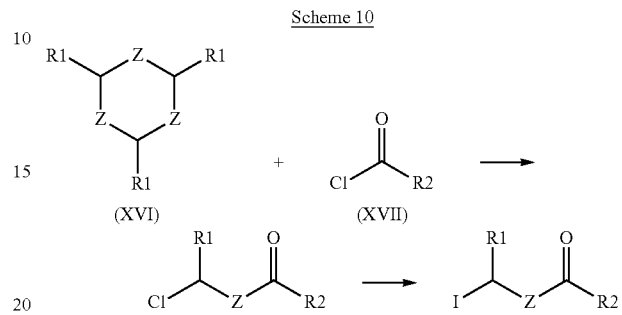

(XVI)    (XVII)

(XVIII)    (XII)

According to scheme 10, the chlorides of formula (XVIII) are available commercially or are prepared from the acid chloride of formula (XVII) by methods selected from those known by a person skilled in the art (Thomas, J. D.; Sloans, K. B.; Synthesis 2008, 2, 272-278 and Majumdar, S.; Sloan, K. B.; *Bioorg. Med. Chem.* 2006, 16, 3590-3594). They comprise the use of a triazene or a trioxane of formula (XVI) in a solvent such as dichloromethane for example.

In a final stage, the iodides of formula (XII) are prepared from the chloride of formula (XVIII) by methods selected from those known by a person skilled in the art. They comprise the use of a chloride of formula (XVIII) and sodium iodide in a solvent such as acetone for example.

The acid chlorides of formula (XVII) and triazines or trioxanes of formula (XVI) are available commercially.

In the case when group Z defined in formula (I) is an oxygen and when group R2 defined in formula (I) is a $C_{1-10}$ alkoxy, the iodides of formula (XII) can be prepared according to reaction scheme 11.

Scheme 11

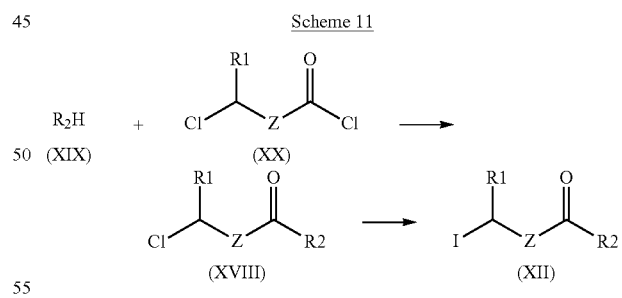

(XIX)    (XX)

(XVIII)    (XII)

According to scheme 11, the chlorides of formula (XVIII) are prepared from the acid chloride of formula (XX) by methods selected from those known by a person skilled in the art (Thomas, J. D.; Sloan, K. B.; *Tetrahedron Lett.* 2007, 48, 109-112). They comprise the use of an alcohol of formula (XIX) and bases such as triethylamine, pyridine, in a solvent such as dichloromethane for example.

In a final stage, the iodides of formula (XII) are prepared from the chloride of formula (XVIII) by methods selected from those known by a person skilled in the art (Thomas, J. D.; Sloan, K. B.; *Tetrahedron Lett.* 2007, 48, 109-112). They comprise the use of a chloride of formula (XVIII) and sodium iodide in a solvent such as acetone for example.

The acid chlorides of formula (XX) and alcohols of formula (XIX) are available commercially.

Investigation of the Sensitivity of the Peroxides Versus Dibenzoyl Peroxide on *Propionibacterium acnes*

Test Principle:

the aim is to evaluate the anti-bacterial activity of the peroxides by measuring the minimum inhibitory concentration (MIC). The MIC is defined as the lowest concentration of product capable of inhibiting all visible growth.

Microbial Strain and Origin:

The sensitivity of the products is investigated on two strains from the Pasteur Institute collection (CIP) of *Propionibacterium acnes* (*P. acnes*):

- *P. acnes* CIP53.117, equivalent to ATCC6919, origin: facial acne lesion (1920), source CRBIP, Pasteur Institute, Paris
- *P. acnes* CIPA179, origin: sebaceous gland (1946), source CRBIP, Pasteur Institute, Paris Tests on the Products:

The products are dissolved at 1280 mg/L in a mixture of absolute ethanol/sterile Tween 80/sterile Wilkins Chalgren broth (May 10, 1985 v/v/v). The dilution ranges used are an adaptation of the method described by the CLSI for methods of dilution in liquid medium. The range consists of 10 concentrations from 2.5 mg/L to 1280 mg/L at intervals of ratio 2.

The suspension of *P. acnes* is prepared in Wilkins Chalgren broth and calibrated at an optical density of about 0.4 at wavelength of 525 nm. It is then diluted to 1/10 in Wilkins Chalgren broth and then put in the test cupules to obtain a final suspension of about $10^5$-$10^6$ CFU/mL in each test cupule.

The solutions of the test products are distributed on a 96-well microplate and incubated at 36° C.±2° C. under anaerobic atmosphere for a minimum of 72 h. The first cupule for which there is no growth visible to the naked eye is regarded as the MIC.

| Strain | Example No. 1 | Example No. 2 |
|---|---|---|
| CIP53.117 | 320 | 160 |
| CIPA179 | 320 | 80 |

EXAMPLE 1 bis(2-acetoxymethoxy)-benzoyl peroxide 1-1: 2-Acetoxymethoxy-benzaldehyde 20 g (185 mmol) of chloromethyl acetate is dissolved in acetone, to which 35 g (230 mmol) of sodium iodide is added. After stirring for 24 hours, 14.8 g (138 mmol) of salicylaldehyde and 38.20 g (276 mmol) of potassium carbonate are dissolved in 100 mL of acetone. The mixture is stirred at room temperature and freshly prepared suspension of iodomethyl acetate is added. After stirring for 24 hours at 50° C., water is added and the mixture is extracted with ethyl acetate. The organic phase is dried over magnesium sulphate, filtered and then concentrated. The residue is purified by silica gel chromatography and eluted with a heptane/ethyl acetate mixture, 7/3. 21.79 g of 2-acetoxymethoxy-benzaldehyde is obtained in the form of a yellow oil at a yield of 98%.

1-2: 2-acetoxymethoxy-benzoic acid 21.79 g (112.2 mmol) of 2-acetoxymethoxy-benzaldehyde and 100 ml (900 mmol) of 2-methyl-2-butene are diluted in 400 ml of tert-butanol. A solution containing 41 g (337 mmol) of sodium hydrogen phosphate and 35 g (393 mmol) of sodium chlorite in 100 ml of water is added dropwise to the reaction mixture, which is stirred for 2 hours at room temperature. The mixture is evaporated under reduced pressure and the residue is dissolved in dichloromethane. The organic phase is washed with water, dried over magnesium sulphate, filtered and concentrated. The white solid obtained is precipitated in heptane at 0° C. The precipitate is filtered, then rinsed with heptane and dried. 14.8 g of 2-acetoxymethoxy-benzoic acid is obtained in the form of white powder at a yield of 63%.

1-3: bis(2-acetoxymethoxy)-benzoyl peroxide 4.9 g (24 mmol) of N,N'-dicyclohexylcarbodiimide is dissolved in 50 ml of diethyl ether at −18° C. 3.37 ml (60 mmol) of an aqueous solution of hydrogen peroxide is added, together with 5 g (24 mmol) of 2-acetoxymethoxy-benzoic acid dissolved in 50 ml of dichloromethane. After stirring for 1 hour at −18° C., 50 ml of diethyl ether is added and the reaction mixture is filtered and then concentrated. The solid obtained is precipitated in diethyl ether and the filtrate is concentrated under reduced pressure. 3 g of bis(2-acetoxymethoxy)-benzoyl peroxide is obtained in the form of white solid at a yield of 60%.

$^1$H NMR/CDCl$_3$: δ=2.31 (s, 6H); 5.94 (s, 4H); 7.20 (m, 4H); 7.60 (t, J=7.6 Hz, 2H); 7.92 (d, 7.5 Hz, 2H)

EXAMPLE 2

(2-acetoxymethoxy-benzoyl)benzoyl peroxide 2-1: Perbenzoic acid 19 g (78 mmol) of dibenzyl peroxide is dissolved in 125 ml of chloroform at −5° C. 2.2 g (94 mmol) of sodium dissolved in 50 ml of methanol under a nitrogen stream, is added dropwise. After stirring for 30 minutes at −5° C., ice water is added and the medium is acidified with an aqueous solution of 2N sulphuric acid. It is extracted with dichloromethane, then the organic phase is dried over magnesium sulphate, filtered and concentrated. 9 g of perbenzoic acid is obtained in the form of white solid at a yield of 83%.

2-2: (2-acetoxymethoxy-benzoyl)benzoyl peroxide 5 g (24 mmol) of 2-acetoxymethoxy-benzoic acid (prepared as described in example 1-2) and 3.3 g (24 mmol) of benzenecarboperoxoic acid are dissolved in 150 mL of diethyl ether/dichloromethane mixture, 6/4. The solution is cooled to 0° C., then 4.9 g (24 mmol) of N,N'-dicyclohexylcarbodiimide dissolved in 85 ml of diethyl ether is added dropwise. After stirring for 3 hours at 0° C., the reaction mixture is filtered and then concentrated. The residue is precipitated in diethyl ether and the filtrate is concentrated under reduced pressure. 5 g of (2-acetoxymethoxy-benzoyl)benzoyl peroxide is obtained in the form of white solid at a yield of 63%.

1H NMR/CDCl$_3$: δ=2.06 (s, 3H); 5.78 (s, 2H); 7.11 (m, 2H); 7.44 (t, J=7.8 Hz; 2H); 7.52 (t, J=7.5 Hz, 1H); 7.59 (t, J=7.8 Hz, 1H); 7.85 (dd, J=1.72 Hz, J=7.7 Hz, 1H); 8.00 (dd, J=8.5 Hz, J=1.4 Hz, 2H).

Evaluation of the Anti-Inflammatory Activity of the Peroxides after a Single Topical Administration in TPA-Induced Ear Oedema.

Principle of the Test:

the aim is to evaluate the anti-inflammatory activity of the peroxides by measuring the thickness of mouse ear after TPA topical application. The anti-inflammatory activity is defined as a inhibition percentage of the TAP-induced ear oedema.

The objective of the study was to demonstrate the anti-inflammatory effect of New peroxide in comparison to BPO (Benzoyl peroxide).

Test on the Products:

An oedema was induced by a single topical application of 20 μl of TPA dissolved in acetone at 0.01%.

Then a single topical application of tested compounds dissolved in TPA solution.

Method of Evaluation:

Ear thickness was measured at T6h.

Results are expressed in percentages based on the inhibition on the oedema induced by the TPA application.

Benzoyl peroxide (BPO) was tested 2 times as a reference peroxide.

|  | Ear oedema | | Inhibition |
| --- | --- | --- | --- |
|  | Mean | Sem | vs TPA (%) |
| TPA 0.01% | 28.80 | 1.67 | N/A |
| TPA 0.01% + BPO 5% | 17.60 | 4.45 | 21.4 |
| TPA 0.01% + BPO 5% | 20.80 | 2.59 | 27.8 |
| TPA 0.01% + Ex2 1% | 20.40 | 2.74 | 19.7 |
| TPA 0.01% + Ex2 2.5% | 14.60 | 2.73 | 42.5 |
| TPA 0.01% + Ex2 5% | 7.20 | 1.85 | 71.7 |
| TPA 0.01% + Ex1 1% | 13.80 | 3.53 | 45.7 |
| TPA 0.01% + Ex1 2.5% | 6.40 | 1.38 | 74.8 |
| TPA 0.01% + Ex1 5% | 4.60 | 0.58 | 81.9 |

CONCLUSION

The aim of this study was to demonstrate the anti-inflammatory effect of New peroxides after a single topical application in the TPA-induced ear oedema mouse model.

Ex n°2 showed a moderate anti-inflammatory effect.

Ex n°1 showed a strong dose-dependent anti-inflammatory effect.

When compared to BPO at 5%, we can ranked the tested compounds as follow:

Ex n°1 at 5% appears slightly better than Ex n°2 at 5% and both are superior compared to BPO 5%.

The invention claimed is:

1. A compound of the following general formula (I):

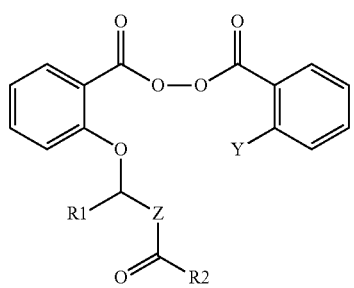

in which:

Z represents an oxygen or the following sequence:

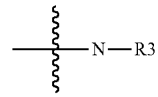

Y represents a hydrogen or the following sequence:

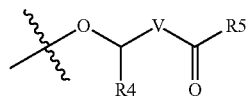

V represents an oxygen or the following sequence:

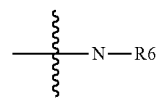

R3 and R6 represent, identically or independently, a hydrogen or a $C_{1-4}$ alkyl R1 and R4 represent, identically or independently, a hydrogen or a $C_{1-4}$ alkyl R2 and R5 represent, identically or independently, a $C_{1-10}$ alkyl or a $C_{1-10}$ alkoxy.

2. The compound as defined by claim 1, wherein:

a. Z represents an oxygen or the following sequence:

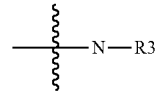

b. Y represents a hydrogen or the following sequence:

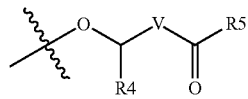

c. V represents an oxygen or the following sequence:

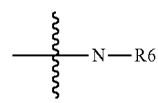

d. R3 and R6 represent, identically or independently, a hydrogen, a methyl or an ethyl e. R1 and R4 represent, identically or independently, a hydrogen or a methyl f. R2 and R5 represent, identically or independently, a $C_{1-4}$ alkyl or a $C_{1-4}$ alkoxy.

3. The compound as defined by claim 1, wherein the compound is selected from the group consisting of bis(2-acetoxymethoxy)-benzoyl peroxide;
(2-acetoxymethoxy-benzoyl)benzoyl peroxide;
bis(2-propionyloxymethoxy)-benzoyl peroxide;
(2-propionyloxymethoxy-benzoyl)benzoyl peroxide;

bis(2-butyryloxymethoxy)-benzoyl peroxide;
(2-butyryloxymethoxy-benzoyl)benzoyl peroxide;
bis(2-pentanoyloxymethoxy)-benzoyl peroxide;
(2-pentanoyloxymethoxy-benzoyl)benzoyl peroxide;
bis(2-isobutyryloxymethoxy)-benzoyl peroxide;
(2-isobutyryloxymethoxy-benzoyl)benzoyl peroxide.;
bis[2-(2,2-dimethyl-propionyloxymethoxy)]-benzoyl peroxide;
[2-(2,2-dimethyl-propionyloxymethoxy)-benzoyl]benzoyl peroxide;
bis[2-(1-acetoxy-ethoxy)]-benzoyl peroxide;
[2-(1-acetoxy-ethoxy)-benzoyl]benzoyl peroxide;
bis(2-ethoxycarbonyloxymethoxy)-benzoyl peroxide;
(2-ethoxycarbonyloxymethoxy-benzoyl)benzoyl peroxide;
bis(2-propoxycarbonyloxymethoxy)-benzoyl peroxide;
(2-propoxycarbonyloxymethoxy-benzoyl)benzoyl peroxide;
bis(2-butoxycarbonyloxymethoxy)-benzoyl peroxide;
(2-butoxycarbonyloxymethoxy-benzoyl)benzoyl peroxide;
bis(2-isopropoxycarbonyloxymethoxy)-benzoyl peroxide;
(2-isopropoxycarbonyloxymethoxy-benzoyl)benzoyl peroxide;
bis(2-tert-butoxycarbonyloxymethoxy)-benzoyl peroxide;
(2-tert-butoxycarbonyloxymethoxy-benzoyl)benzoyl peroxide;
bis [2-(ethoxycarbonylamino-methoxy)]-benzoyl peroxide;
[2-(ethoxycarbonylamino-methoxy)-benzoyl]benzoyl peroxide;
bis (2-([ethoxycarbonyl-ethyl-amino]-methoxy])-benzoyl peroxide;
(2-[(ethoxycarbonyl-ethyl-amino)methoxy]-benzoyl)benzoyl peroxide;
bis(2-[(ethoxycarbonyl-methyl-amino)-methoxy])-benzoyl peroxide;
(2-[(ethoxycarbonyl-methyl-amino)-methoxy]benzoyl)benzoyl peroxide;
bis(2-[(methyl-propoxycarbonyl-amino)-methoxy])-benzoyl peroxide;
(2-[(methyl-propoxycarbonyl-amino)-methoxy]-benzoyl)benzoyl peroxide;
bis(2-[(butoxycarbonyl-methyl-amino)methoxy])-benzoyl peroxide;
(2-[(butoxycarbonyl-methyl-amino)-methoxy]-benzoyl)benzoyl peroxide;
bis(2-[(isopropoxycarbonyl-methyl-amino)-methoxy])-benzoyl peroxide;
(2-[(isopropoxycarbonyl-methyl-aminoymethoxy]-benzoyl) benzoyl peroxide;
bis(2-tert-butoxycarbonyl-methyl-amino)methoxyp-benzoyl peroxide;
(2-[(tert-butoxycarbonyl-methyl-amino)-methoxy]-benzoyl) benzoyl peroxide;
bis[2-(1-ethoxycarbonyloxy-ethoxy)]-benzoyl peroxide; and
[2-(1-ethoxycarbonyloxy-ethoxy)-benzoyl]benzoyl peroxide.

4. The compound as defined by claim 1, wherein the compound is a medicinal product.

5. The compound as defined by claim 1, wherein the compound is effective to treat pathologies or disorders associated with the presence of *Propionibacterium acnes*.

6. A cosmetic composition comprising an effective amount of the compound defined by claim 1, wherein the effective amount of the compound inhibits proliferation of a pathogenic germ involved in development of an acne-type skin disorder.

7. The composition of claim 6, wherein a. Z represents an oxygen or the following sequence:

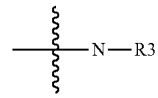

b. Y represents a hydrogen or the following sequence:

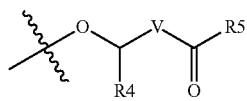

c. V represents an oxygen or the following sequence:

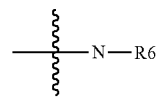

d. R3 and R6 represent, identically or independently, a hydrogen, a methyl or an ethyl
e. R1 and R4 represent, identically or independently, a hydrogen or a methyl
f. R2 and R5 represent, identically or independently, a $C_{1-4}$ alkyl or a $C_{1-4}$ alkoxy.

8. The composition of claim 6, wherein the compound is selected from the group consisting of:
bis(2-acetoxymethoxy)-benzoyl peroxide;
(2-acetoxymethoxy-benzoyl)benzoyl peroxide;
bis(2-propionyloxymethoxy)-benzoyl peroxide;
(2-propionyloxymethoxy-benzoyl)benzoyl peroxide;
bis(2-butyryloxymethoxy)-benzoyl peroxide;
(2-butyryloxymethoxy-benzoyl)benzoyl peroxide;
bis(2-pentanoyloxymethoxy)-benzoyl peroxide;
(2-pentanoyloxymethoxy-benzoyl)benzoyl peroxide;
bis(2-isobutyryloxymethoxy)-benzoyl peroxide;
(2-isobutyryloxymethoxy-benzoyl)benzoyl peroxide;
bis[2-(2,2-dimethyl-propionyloxymethoxy)]-benzoyl peroxide;
[2-(2,2-dimethyl-propionyloxymethoxy)-benzoyl]benzoyl peroxide;
bis[2-(1-acetoxy-ethoxy)]-benzoyl peroxide;
[2-(1-acetoxy-ethoxy)-benzoyl]benzoyl peroxide;
bis(2-ethoxycarbonyloxymethoxy)-benzoyl peroxide;
(2-ethoxycarbonyloxymethoxy-benzoyl)benzoyl peroxide;
bis(2-propoxycarbonyloxymethoxy)-benzoyl peroxide;
(2-propoxycarbonyloxymethoxy-benzoyl)benzoyl peroxide;
bis(2-butoxycarbonyloxymethoxy)-benzoyl peroxide;
(2-butoxycarbonyloxymethoxy-benzoyl)benzoyl peroxide;
bis(2-isopropoxycarbonyloxymethoxy)-benzoyl peroxide;
(2-isopropoxycarbonyloxymethoxy-benzoyl)benzoyl peroxide;
bis(2-tert-butoxycarbonyloxymethoxy)-benzoyl peroxide;

(2-tert-butoxycarbonyloxymethoxy-benzoyl)benzoyl peroxide;
bis[2-(ethoxycarbonylamino-methoxy)]-benzoyl peroxide;
[2-(ethoxycarbonylamino-methoxy)-benzoyl]benzoyl peroxide;
bis(2-([ethoxycarbonyl-ethyl-amino)methoxy])-benzoyl peroxide;
(2-[(ethoxycarbonyl-ethyl-amino)-methoxy]-benzoyl) benzoyl peroxide;
bis(2-[(ethoxycarbonyl-methyl-amino)-methoxy])-benzoyl peroxide;
(2-[(ethoxycarbonyl-methyl-amino)-methoxy]-benzoyl) benzoyl peroxide;
bis(2-[(methyl-propoxycarbonyl-amino)methoxy])-benzoyl peroxide;
(2-[(methyl-propoxycarbonyl-amino)-methoxy]-benzoyl) benzoyl peroxide;
bis(2-[(butoxycarbonyl-methyl-amino)-methoxy])-benzoyl peroxide;
(2-[(butoxycarbonyl-methyl-amino)methoxy]-benzoyl) benzoyl peroxide;
bis(2-[(isopropoxycarbonyl-methyl-amino)-methoxy])-benzoyl peroxide;
(2-[(isopropoxycarbonyl-methyl-amino)methoxy]-benzoyl)benzoyl peroxide;
bis(2-[(tert-butoxycarbonyl-methyl-amino)methoxy]-benzoyl peroxide;
(2-[(tert-butoxycarbonyl-methyl-amino)-methoxy]-benzoyl)benzoyl peroxide;
bis[2-(1-ethoxycarbonyloxy-ethoxy)]benzoyl peroxide; and
[2-(1-ethoxycarbonyloxy-ethoxy)-benzoyl]benzoyl peroxide.

9. The composition of claim 6, wherein the acne-type skin disorder is *P. acnes*.

* * * * *